United States Patent [19]

Lenzner

[11] Patent Number: 5,310,947
[45] Date of Patent: May 10, 1994

[54] PROCESS FOR THE PRODUCTION OF TETRONIC ACID ALKYL ESTERS

[75] Inventor: Joachim Lenzner, Visp, Switzerland

[73] Assignee: Lonza Ltd., Gampel/Valais, Switzerland

[21] Appl. No.: 72,955

[22] Filed: Jun. 8, 1993

[30] Foreign Application Priority Data

Jun. 11, 1992 [CH] Switzerland .................. 1846/92

[51] Int. Cl.$^5$ .................. C07D 307/32; C07D 307/33
[52] U.S. Cl. .................................................. 549/313
[58] Field of Search .......................................... 549/313

[56] References Cited

U.S. PATENT DOCUMENTS

| | | | |
|---|---|---|---|
| 4,780,545 | 10/1988 | Meul et al. | 548/543 |
| 4,788,294 | 11/1988 | Duc et al. | 548/544 |
| 4,880,940 | 11/1989 | Meul et al. | 548/544 |
| 5,144,047 | 9/1992 | Duc et al. | 549/429 |

OTHER PUBLICATIONS

Pelter et al., J. Chem. Soc. Perkin Trans I, (1987), pp. 717 to 742.
Duc et al., Synthesis (Apr. 1992), pp. 391 to 394.

*Primary Examiner*—C. Warren Ivy
*Assistant Examiner*—Ba K. Trinh
*Attorney, Agent, or Firm*—Fisher, Christen & Sabol

[57] ABSTRACT

A new process for the production of tetronic acid alkyl esters of the general formula:

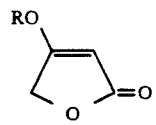

starting from 4-haloacetoacetic acid alkyl esters of the general formula:

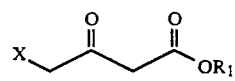

The 4-haloacetoacetic acid alkyl esters of general formula II are converted in a first step with a dialkylsulfite of the general formula:

$(RO)_2S=O$   III in the presence of a strong acid into a 4-halo-3-alkoxy-but-2E-enoic acid alkyl ester of the general formula:

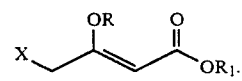

The latter is cyclized in a second step with a formate and a strong acid to the end product according to formula I.

17 Claims, No Drawings

PROCESS FOR THE PRODUCTION OF TETRONIC ACID ALKYL ESTERS

BACKGROUND OF THE INVENTION

1. Field Of The Invention

The invention relates to a new process for the production of tetronic acid alkyl esters of the general formula:

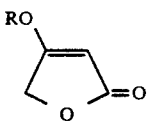

wherein R means a $C_1$–$C_6$-alkyl group, starting from 4-haloacetoacetic acid alkyl esters of the general formula:

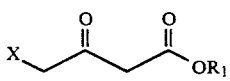

wherein X means chlorine or bromine and $R_1$ means a $C_1$–$C_6$-alkyl group.

2. Background Art

To date several processes for the production of tetronic acid alkyl esters are known.

For example, European Published Patent Application No. 409,147 describes a process for the production of tetronic acid alkyl esters starting from 4-chloro-3-ethoxy-but-2E-enoic acid alkyl esters. The 4-chloro-3-ethoxy-but-2E-enoic acid alkyl esters are reacted at temperatures between 190° and 260° C. under an inert gas atmosphere without a solvent to the corresponding tetronic acid alkyl ester. A serious drawback of such process is that it cannot be performed on an industrial scale and that chloroethane accumulates as a waste product to be disposed of.

BROAD DESCRIPTION OF THE INVENTION

The main object of the invention is to provide an ecological process, feasible on an industrial scale, for the production of tetronic acid alkyl esters. This main object is achieved with the new process of the invention.

Other objects and advantages of the invention are set out herein or are obvious herefrom to one skilled in the art. The objects and advantages of the invention are achieved by the process of the invention.

According to the invention the process is performed so that, in a first step, a 4-halo-acetoacetic acid alkyl ester of the general formula:

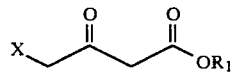

wherein X is chlorine or bromine and $R_1$ is a $C_1$–$C_6$-alkyl group, is converted with a dialkylsulfite of the general formula:

$(RO)_2S=O$  III wherein R is a $C_1$–$C_6$-alkyl group, into the corresponding intermediately formed ketal ester. The latter is converted in the presence of a strong acid into a 4-halo-3-alkoxy-but-2E-enoic acid alkyl ester of the general formula:

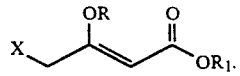

wherein X, R and $R_1$ have the above-mentioned meanings. The latter is then cyclized in a second step with a formate and a strong acid to the end product according to the genera formula:

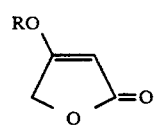

Tetronic acid alkyl esters are, e.g., valuable intermediate products for the production of pharmaceutical active ingredients [Pelter et al., J. Chem. Soc. Perkin Trans I, (1987), pages 717 to 742].

DETAILED DESCRIPTION OF THE INVENTION

The feedstock of the production process of 4-haloacetoacetic acid-$C_1$–$C_6$-alkyl esters can be produced on an industrial scale starting from diketene and from the corresponding halogen over the corresponding acid chloride.

Suitable useful representatives of the 4-halo-acetoacetic acid alkyl esters are 4-halo-acetoacetic acid methyl, ethyl, propyl, isopropyl or butyl esters, in which halogen is a bromine or chlorine atom. Preferably 4-chloroacetoacetic acid ethyl ester is used.

Suitably the dialkylsulfite of formula III is formed in situ by reaction of thionyl chloride with the corresponding aliphatic alcohol. As the aliphatic alcohols, methanol, ethanol, propanol, isopropanol or butanol can be used. Preferably ethanol is used and consequently diethylsulfite results as the dialkylsulfite. Suitably the alcohol is used in excess for in situ formation of the dialkylsulfite, preferably in an amount of 2.5 to 4 mol per mol of thionyl chloride.

Up to the formation of the ketal ester the reaction in the first step is suitably performed at a temperature of −10° to 60° C.

Then the reaction up to 4-halo-3-alkoxy-but-2E-enoic acid alkyl ester of formula IV is performed in the presence of a strong acid, at a suitable temperature of 60° to 120° C. Suitably, in this way, that the lower boiling components resulting in the reaction are removed by distillation. As the strong acids, for example, methanesulfonic acid or p-toluenesulfonic acid are suitable. Preferably methanesulfonic acid is used as the strong acid. Suitably the strong acid is used in a catalytic amount of 20 to 30 mmol per mol of 4-haloacetoacetic acid alkyl ester of formula II.

After a usual reaction time of 3 to 6 hours, the 4-halo-3-alkoxy-but-2E-enoic acid alkyl ester according to the general formula:

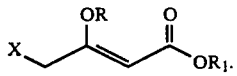

can then be isolated or used directly for the second step. Preferably the 4-halo-3-alkoxy-but-2E-enoic acid alkyl ester is used directly, without isolation, for the second step.

In the second step, the cyclization of 4-halo-3-alkoxy-but-2E-enoic acid alkyl ester to the tetronic acid alkyl ester is performed with a formate and a strong acid. As the strong acids, the same ones as previously described in the first step can be used. As the formates, alkali or alkaline-earth formates can be used. As the alkali formate, for example, sodium or potassium formate can be used. As the alkaline-earth formate, for example, magnesium or calcium formate can be used. Suitably the formates are used in excess relative to the 4-halo-3-alkoxy-but-2E-enoic acid alkyl ester of formula IV. Preferably the excess is 5 to 15 percent by weight relative to the 4-halo-3-alkoxy-but-2E-enoic acid alkyl ester. As the solvent in the second step, polar aprotic solvents can be used. As the polar aprotic solvent, suitably a mixture of dimethylformamide and water is used. Preferably dimethylformamide is mixed with water in a molar ratio of dimethylformamide to water of 1.5 to 1.8. The reaction in the second step is suitably performed at a temperature of 110° to 130° C., preferably of 115° to 120° C.

After a usual reaction time of 10 to 15 hours the tetronic acid alkyl ester can then be isolated in good yields according to methods usual to one skilled in the art.

EXAMPLE

PRODUCTION OF TETRONIC ACID ETHYL ESTERS

4-Chloroacetoacetic acid ethyl ester (447.0 kg; 2.7 kmol) and absolute ethanol (621.4 l) were introduced under inert gas atmosphere. Thionyl chloride (349.2 kg; 2.94 kmol) was then added at a temperature between $-5°$ and $-10°$ C. so that the temperature did not rise above $+20°$ C. After the addition of thionyl chloride, the temperature was raised from 20° to 60° C. (0.3° C./min), the methanesulfonic acid (2.56 kg; 26 mol) was added and the temperature raised from 60° to 120° C. The ethanol thusly evaporated was collected. Then the ethanol resulting in the conversion from the ketal ester to the 4-chloro-3-ethoxy-but-2E-enoic acid ethyl ester was distilled off at a temperature of 110° to 120° C. Then, all of this was cooled to 40° C. and, for the second step, methanesulfonic acid (2.5 kg; 26 mol), sodium formate (189.2 kg; 2.74 mol), dimethylformamide (513.4 l) and water (75.8 l) were added under inert gas atmosphere. After raising the internal temperature to 120° C., the reaction mixture was stirred for 12 hours, and the lower boiling components resulting in the reaction were removed by distillation. Then dimethylformamide was removed by distillation at 30 to 50 mbar. The reaction mixture was suspended with acetone (500 l), filtered and rewashed again with acetone. Then the acetone was distilled off. The solution containing tetronic acid ethyl ester was cooled to 20° C. 328.2 kg of tetronic acid ethyl ester (crude) with a content of 75 percent (according to GC), corresponding to a yield of 75 percent, was obtained.

What is claimed is:

1. A process for the production of a tetronic acid alkyl esters of formula:

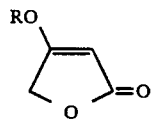

wherein R is a $C_1$–$C_6$-alkyl group, comprising, in a first step, converting a 4-halo-acetoacetic acid alkyl ester of formula:

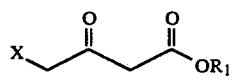

wherein X is chlorine or bromine and $R_1$ is a $C_1$–$C_6$-alkyl group, with a dialkylsulfite of formula:

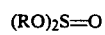

wherein R has the above-mentioned meaning, into the corresponding intermediately formed ketal ester, converting the corresponding intermediately-formed ketal ester in the presence of a strong acid into a 4-halo-3-alkoxy-but-2E-enoic acid alkyl ester of formula:

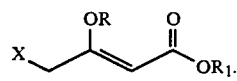

wherein X, R and $R_1$ have the above-mentioned meanings, and then cyclizing in a second step, the 4-halo-3-alkoxy-but-2E-enoic acid alkyl ester with a formate and a strong acid to the tetronic acid alkyl ester of formula I.

2. The process according to claim 1 wherein in the first step 4-chloroacetoacetic acid ethyl ester is used as the 4-halo-acetoacetic acid alkyl ester of formula II.

3. The process according to claim 1 wherein in the first step, diethylsulfite is used as the dialkylsulfite of formula III.

4. The process according to claim 3 wherein, in the first step, the dialkylsulfite of formula III is produced in situ by reaction of thionyl chloride with the corresponding aliphatic alcohol.

5. The process according to claim 4 wherein, in the first step, the reaction up to the intermediately-formed ketal ester is performed at a temperature of $-10°$ to 60° C. and then the reaction up to 4-halo-3-alkoxy-but-2E-enoic acid alkyl ester of formula IV is performed at a temperature of 60° to 120° C.

6. The process according to claim 5 wherein, in the first and second steps, methanesulfonic acid or p-toluenesulfonic acid is used as the strong acid.

7. The process according to claim 6 wherein in the second step an alkali or alkaline-earth formate is used as the formate.

8. The process according to claim 7 wherein the reaction in the second step is performed in a mixture of dimethylformamide and water.

9. The process according to claim 8 wherein the reaction in the second step is performed at a temperature of 110° to 130° C.

10. The process according to claim 9 wherein the reaction is performed according to formula IV without isolation of the intermediate product.

11. The process according to claim 1 wherein, in the first step, the dialkylsulfite of formula III is produced in situ by reaction of thionyl chloride with the corresponding aliphatic alcohol.

12. The process according to claim 1 wherein, in the first step, the reaction up to the intermediately-formed ketal ester is performed at a temperature of −10° to 60° C. and then the reaction up to 4-halo-3-alkoxy-but-2E-enoic acid alkyl ester of formula IV is performed at a temperature of 60° to 120° C.

13. The process according to claim 1 wherein, in the first and second steps, methanesulfonic acid or p-toluenesulfonic acid is used as the strong acid.

14. The process according to claim 1 wherein in the second step an alkali or alkaline-earth formate is used as the formate.

15. The process according to claim 1 wherein the reaction in the second step is performed in a mixture of dimethylformamide and water.

16. The process according to claim 1 wherein the reaction in the second step is performed at a temperature of 110° to 130° C.

17. The process according to claim 1 wherein the reaction is performed according to formula IV without isolation of the intermediate product.

* * * * *